United States Patent [19]

Czaja et al.

[11] 3,953,520

[45] Apr. 27, 1976

[54] CHEMICAL COMPOUNDS AND PROCESSES

[75] Inventors: Robert F. Czaja, Scotch Plains; Seemon H. Pines, Murray Hill; Newton L. Abramson, Edison, all of N.J.

[73] Assignee: Merck & Co., Inc., Rahway, N.J.

[22] Filed: Feb. 24, 1975

[21] Appl. No.: 552,486

Related U.S. Application Data

[63] Continuation-in-part of Ser. No. 426,865, Dec. 20, 1973, abandoned.

[52] U.S. Cl.............................. 260/609 E; 260/609 F; 260/607 A; 260/611 A; 260/607 R
[51] Int. Cl.² ........................................ C07C 149/34
[58] Field of Search........ 260/651 HA, 609 E, 609 F

[56] References Cited

UNITED STATES PATENTS

| 2,951,100 | 8/1960 | Adams et al. ................ 260/651 HA |
| 3,217,048 | 11/1965 | Garmaise et al. ............ 260/651 HA |
| 3,284,518 | 11/1966 | Ayers et al. .................. 260/651 HA |
| 3,676,514 | 7/1972 | Rosenthal .................... 260/651 HA |

*Primary Examiner*—Lewis Gotts
*Assistant Examiner*—D. R. Phillips
*Attorney, Agent, or Firm*—Mario A. Monaco; Harry E. Westlake, Jr.

[57] ABSTRACT

Haloalkyl derivatives of aromatic compounds are prepared via reaction with dialkoxy or aralkoxy alkanes in the presence of a Lewis acid.

7 Claims, No Drawings

CHEMICAL COMPOUNDS AND PROCESSES

RELATED CASES

This application is a continuation-in-part of U.S. Ser. No. 426,865 filed December 20, 1973, now abandoned.

DESCRIPTION OF THE INVENTION

This invention relates to a novel process for the preparation of haloalkyl derivatives of aromatic compounds via reaction of a di-(alkoxy or aralkoxy) alkane with an aromatic compound in the presence of a Lewis acid. These haloalkyl compounds are useful as intermediates in the preparation of cosmetics, pesticides and pharmaceutical compounds.

BACKGROUND OF THE INVENTION

In the past, haloalkylation of aromatic compounds such as benzene and its derivatives was usually carried out by reaction with a haloalkyl ether or by reaction with aldehydes and hydrochloric acid such as is described in "Friedel-Crafts and Related Reactions", volume II, part 2, page 659, G. Oloh, Editor. The drawback to such procedures has been the lack of specificity of isomers obtained and frequently poor yields. For example, the previous preparation in the literature, (Journal of Organic Chemistry, 17, 350, 1952), for p-methylthiobenzyl chloride from thioanisole reports poor yields of product. That product, in fact, contains a high proportion of ortho isomer. We have found a novel process wherein an aromatic compound having an alkylthio group therein is haloalkylated with a di-(alkoxy or aralkoxy) alkane in the presence of a Lewis acid containing at least one halogen atom. We have further found that by this process the preparation of p-methythiobenzyl chloride from thioanisole, for example, is accomplished in a much higher yield and with substantially higher isomeric purity than in its previous preparation.

DETAILS OF THE INVENTION

It is an object of this invention to prepare haloalkyl (i.e., halomethyl or α-haloethyl) derivatives of aromatic compounds by a completely new process which leads to good yields of desired product. In accordance with this invention, compounds of the following formula may be prepared:

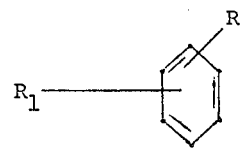

wherein Y is —$CH_2$ or —$CH$-$CH_3$; X is halogen (chloro, bromo, fluoro); R and $R_1$ may each be hydrogen, $C_{1-5}$ alkyl, $C_{1-5}$ alkylthio, $C_{1-5}$ alkylsulfinyl, $C_{1-5}$ alkylsulfonyl, $C_{1-5}$ alkoxy, hydroxy or halo (chloro, bromo, fluoro), at least one of said R or $R_1$ being an alkylthio. Preferably, X is chloro or bromo, R and $R_1$ are each hydrogen, $C_{1-5}$ alkyl (methyl, ethyl, butyl), chloro, fluoro, $C_{1-5}$ alkylthio (methylthio, ethylthio, propylthio) and $C_{1-5}$ alkoxy (methoxy, ethoxy, propoxy) and Y is -$CH_2$.

In the most preferred aspect of this invention, X is chloro, R and $R_1$ are each hydrogen, $C_{1-5}$ alkyl, $C_{1-5}$ alkylthio, $C_{1-5}$ alkoxy or halo such as methylthio, methoxy or chloro and Y is —$CH_2$; especially one of R and $R_1$ is hydrogen, the other alkylthio. Representative compounds prepared in accordance with this invention are: p-methylthiobenzyl bromide; p-methylthiobenzyl chloride; 3-methyl-4-methylthiobenzyl chloride; and α-(p-methylthio)phenethyl chloride.

The process of this invention leads to ortho and para isomers of the haloalkyl final product. The ratio of isomers for any particular product will naturally depend upon the reaction conditions such as the catalyst used as well as the nature of the starting material. When it is desired to separate the isomers, normal techniques may be used such as fractional distillation.

In the process of this invention a compound of the formula:

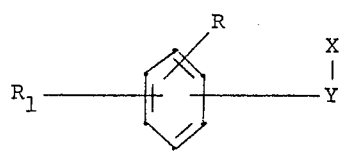

is reacted with a dialkoxy or di-aralkoxy alkane of the formula:

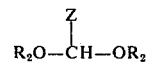

wherein Z is hydrogen or methyl, $R_2$ is $C_{1-5}$ alkyl or $C_{7-10}$ aralkyl such as methyl, ethyl, propyl, benzyl or phenethyl and each $R_2$ may be the same or different but preferably are the same and a Lewis acid containing a halogen such as Al, Sn, Sb, Ti, Zr, Hf, Fe, Ga, B or P halides or oxyhalides with subsequent agueous cleavage of the formed complex. Preferably, the reaction is carried out using a di $C_{1-5}$ alkoxymethane or di 1,1-$C_{1-5}$ alkoxyethane and especially dimethoxymethane or 1,1-dimethoxyethane and a Lewis acid halide such as Al $Cl_3$, Ti $Cl_4$, Sn $Cl_4$ or Fe $Cl_3$ but especially Al $Cl_3$.

The reaction may be carried out with or without a solvent but preferably with a solvent. For such purposes, one may use various inert solvents such as halogenated alkanes of preferably up to 5 carbon atoms (ethylene dichloride, carbon tetrachloride, chloroform, methylene dichloride); halogenated alkenes of preferably up to 5 carbon atoms (trichloroethylene); nonreactive aromatic (benzene type) solvents such as nitrobenzene or trichlorobenzene; ethers containing preferably up to 6 carbon atoms (tetrahydrofuran, dioxane, dimethylether, 1,2-dimethoxyethane); aliphatic hydrocarbons of up to 15 carbon atoms such as alkanes of up to 10 carbon atoms (hexane, nonane) and cycloalkanes of up to 8 carbons atoms such as methylcyclohexane; nitroalkanes such as nitromethane or carbon disulfide. In the preferred aspect of the invention halogenated alkanes are employed as solvent and especially ethylene dichloride.

The concentration of reactants is not critical, however, generally higher yields are obtained with a ratio of Lewis acid to aromatic reactant above 1. Accordingly, a mole ratio of Lewis acid to aromatic reactant may be from about 1:1 to about 4:1 and preferably between about 2–3:1. Similarly, the concentration of dialkoxy or di-aralkoxyalkane to aromatic reactant is not critical and one may readily employ a mole ratio between about 0.5 to 2:1 and preferably about 1:1. The temperature and time of reaction may suitably be between about −70° to 80°C and the reaction time from 1 to 24 hours. Preferably, however, the reaction is carried out at a temperature of from about 0° to 40°C for about 4 to 16 hours and especially about 10° to 25°C. The order of addition of reactants is not critical and therefore one may add any one reactant to the other two or any two mixed reactants to the other one. It has been found, however, to be preferable to add the aromatic reactant to the mixture of Lewis acid and dialkoxy (or aralkoxy-)alkane. After the reaction is at least substantially completed, the product in the form of its Lewis acid complex is cleaved to the desired product by contacting the reaction mixture with an aqueous solution and preferably water. This quenching is carried out in a generally known manner. For example, water may be added to the reaction mixture or the reaction mixture added to the water at a temperature of from about 0° to about 70°C (preferably 20°–40°C) over any convenient length of time. The amount of water is not critical. All that is necessary for substantial cleavage of the complex is about a mole of water for every mole of Lewis acid used. Conveniently, however, a sufficient excess of water is used in order to obtain ease of handling of the reaction mixture.

In the most preferred aspect of the invention thioanisole is reacted in accordance with this invention to form p-methylthiobenzyl chloride containing less than one part in 100 of its ortho isomer. The p-methylthiobenzyl chloride is useful as an intermediate in the preparation of 5-fluoro-2-methyl-1-(p-methylsulfinylbenzylidene)-indenyl-3-acetic acid, an anti-inflammatory compound as described in U.S. Pat. No. 3,654,349. The p-methylthiobenzyl chloride prepared by the process of this invention is converted to a Grignard reagent which is subsequently reacted under Grignard conditions with 5-fluoro-2-methyl-1-indanone to form 5-fluoro2-methyl-1-(p-methylthiobenzyl)-indene which compound is in turn reacted with glyoxylic acid to form the corresponding 5-fluoro-2-methyl-1-(p-methylthiobenzyl)-indenylidene-3-acetic acid, then isomerized and finally oxidized to 5-fluoro-2-methyl-1-(p-methylsulfinylbenzylidene)-indenyl-3-acetic acid.

The following examples are given by way of illustration:

EXAMPLE 1 p-Methylthiobenzyl chloride

To a stirred mixture of 587 g. (4.4 moles) of anhydrous aluminum chloride in 2,000 ml. of 1,2-dichloroethane is added 168 g. (2.2 moles) of dimethoxymethane over a 45 minute period at 0°–10°C. After this, 248 g. (2 moles) of thioanisole was added similarly. The reaction was brought to 25°C and held at that temperature six hours. It was then quenched with 2,100 ml. of water, keeping the temperature below 25°C. The organic layer and a 1,2-dichloroethane extract of the aqueous phase was concentrated to give an oil which contained 240.8 g. (74.4%) of p-methylthiobenzyl chloride. The oil contained less than 2 grams of o-methylthiobenzyl chloride.

Similarly when stannic chloride, zirconium oxychloride, hafnium tetrachloride, boron trichloride, ferric chloride or antimony chloride are used in place of aluminum chloride in the above example, the desired product is obtained.

Similarly when antimony bromide, stannic bromide or aluminum bromide is used in place of aluminum chloride in the above example, there is obtained p-methylthiobenzyl bromide.

Similarly when diethoxymethane, di-n-propyloxymethane or dibenzyloxymethane is used in place of dimethoxymethane in the above example, the desired product is obtained.

EXAMPLE 2 p-Methylthiobenzyl chloride

A solution of 24.8 g. (0.20 mole) of thioanisole in 180 ml. of ethylene dichloride was cooled to −5°C in an ice-methanol bath. 48 Ml. (83.6 g., 0.44 mole) of titanium tetrachloride was added dropwise over 15 minutes while maintaining the temperature at 0°–5°C. Another 10 ml. of ethylene dichloride was employed to wash forward the last quantities of titanium tetrachloride. The solution was cooled to −5°C again and 16.8 g. (0.22 mole) of methylal was added over 15 minutes while holding the temperature at 0–5°C. The reaction was stirred for 24 hours at 0–5°C and was quenched in 250 g. of ice. The organic layer was separated and the aqueous layer was extracted with 2 × 100 ml. of ethylene dichloride. The combined organic layers were dried over anhydrous magnesium sulfate and concentrated in vacuo at 50°–60°C to give 31.6 g. of crude product. Quantitative vpc analysis showed the product to contain a 64% yield of p-methylthiobenzyl chloride and a 5% yield of the ortho isomer.

Similarly when an equivalent amount of ortho-methylthiotoluene is used in place of thioanisole, there is obtained 3-methyl-4-methylthiobenzyl chloride.

Similarly when an equivalent amount of stannic chloride, zirconium oxychloride, hafnium tetrachloride, boron trichloride, ferric chloride or antimony chloride is used in place of titanium tetrachloride in the above example, the desired product is obtained.

Similarly when diethoxymethane, di-n-propyloxymethane or dibenzyloxymethane is used in place of dimethoxymethane in the above procedure, the desired product is obtained.

EXAMPLE 3

α-(p-Methylthio)phenethyl chloride 1,1-Dimethoxyethane, 49.56 g. (0.55 mole) was added to a mixture of 147 g. (1.1 mole) of anhydrous aluminum chloride in 500 ml. of 1,2-dichloroethane over 45 minutes at 0°–10°C. 62 G. (0.50 mole) of thioanisole was then added in a similar manner. The reaction was warmed to 25°C and held at that temperature for 6 hours. The solution was then quenched with 500 ml. of water while holding the temperature below 25°C. The organic layer was separated from the aqueous layer. The aqueous layer was washed with 100 ml. of 1,2-dichloroethane. The combined organic extracts were concentrated in vacuo to give α-(p-methylthio)-phenethyl chloride.

Similarly when stannic chloride, zirconium oxychloride, hafnium tetrachloride, boron trichloride, ferric chloride or antimony chloride are used in place of aluminum chloride in the above example, the desired product is obtained.

Similarly when 1,1-diisopropyloxyethane, 1-1-dibenzyloxyethane or 1,1-diethoxyethane is used in place of 1,1-dimethoxyethane, the desired product is obtained.

EXAMPLE 4

α-Methyl-3-fluorocinnamic acid

A mixture of 49.6 g. (0.4 mole) of meta-fluorobenzaldehyde, 66 ml. (0.51 mole) of propionic anhydride and 38.4 g. (0.4 mole) of sodium propionate were heated at 135°C for 19 hours. The reaction was cooled and to it was added a liter of 1 normal potassium hydroxide and the mixture was extracted with ether. The aqueous phase was freed of residual ether and acidified to pH 2 with hydrochloric acid. The product which crystallized was filtered and dried to give 51.5 grams of α-methyl-3-fluorocinnamic acid, melting point 95°–97°C.

EXAMPLE 5

α-Methyl-3-fluorohydrocinnamic acid 15.6 G. of the above product from Example 4 was hydrogenated at 40 pounds per square inch in 800 ml. of methanol with 3 g. of platinum oxide catalyst. After the theoretical uptake of hydrogen, the hydrogenation was stopped. The catalyst was removed by filtration and the solvent removed in vacuo giving a theoretical yield of the desired product, α-methyl-3-fluorohydrocinnamic acid.

EXAMPLE 6

5-Fluoro-2-methyl-1-indanone

The product of Example 5 is heated with 10 times its weight of polyphosphoric acid at 80°–90°C. for 2 hours. The liquid is poured into 1 l. of ice water, stirred for one-half hour and extracted with three 100 ml. portions of ether. The combined extracts are washed with water and sodium bicarbonate solution until the ether phase is neutral, after which the extract is dried over sodium sulfate and concentrated to leave 5-fluoro-2-methyl-1-indanone as a yellowish oil, b.p. 60°C/0.15 mm.

EXAMPLE 7

5-Fluoro-2-methyl-1-(p-methylthiobenzyl)-indene 13.44 G. (0.56 mole) of magnesium turnings were placed in a dried flask under $N_2$ with 125 ml. of ether and a crystal of iodine. 6 Ml. of 65 ml. solution of 24.2 g. (0.14 mole) of p-methylthiobenzyl chloride in ether was added. After 3 to 5 minutes of stirring, the iodine color disappeared and the reaction began. After aging for 5 minutes, the rest of the benzyl chloride was added dropwise over 45 minutes. It was rinsed in with 10 ml. of ether and the reaction aged for 2 hours with stirring. 21 G. (0.128 mole) of 5-fluoro-2-methyl-1-indanone dissolved in 50 ml. of ether was added dropwise over 30 minutes. After aging for 1 hour, the milky supernatent mixture was decanted from the magnesium into 100 ml. of acetic acid. The flask and residual magnesium were rinsed into the acid solution with 4 × 50 ml. of benzene. 200 Ml. of water were added, the layers were separated and the organic layer was washed with 5 × 200 ml. water. It was stripped to dryness after drying over $Na_2SO_4$. The crude reaction product is crystallized from hexane to give pure 5-fluoro-2-methyl-1-(p-methylthiobenzyl)-indene, melting point 58°–59°C.

EXAMPLE 8

5-Fluoro-2-methyl-1-(p-methylthiobenzyl)-indenylidene-3-acetic acid

To 41.8 g. (147 mmoles) of the preceeding indene (from Example 7) is added 150 ml. of methanolic Triton B solution (53.2 g., dry basis; 317.5 mmoles) and the batch, under a nitrogen atmosphere, is brought to 45°C. 14.63 G glyoxylic acid (198 mmoles) is added and the batch, which warms to 65°C, is brought back to 50°C and aged 1 hour. It is then diluted with 250 ml. of water and acidified with dilute sulfuric acid. The product obtained in 90% yield is recrystallized to give the pure subject product, melting point 185.5° to 188°C.

EXAMPLE 9

5-Fluoro-2-methyl-1-(p-methylthiobenzylidene)-indenyl-3-acetic acid

A suspension of 34.2 g. of 5-fluoro-2-methyl-1-(p-methylthiobenzyl)-indenylidene-3-acetic acid (from Example 8) in 342 ml. of glacial acetic acid and 137 ml. of concentrated HCl was stirred under a nitrogen atmosphere at 90°C for 10 hours. The reaction was cooled over 2-3 hours to room temperature and aged an additional 3 hours at 20°–25°C. The batch was filtered, washed with 70:30 acetic acid-water (ca. 100 ml.) then water-washed to remove excess acid. There was obtained 93% of product, meltint point 180°–183°C.

EXAMPLE 10

5-Fluoro-2-methyl-1-(p-methylsulfinylbenzylidene)-indenyl-3-acetic acid

17 G. (50 mmoles) of the product from Example 9 is stirred in 175 ml. of chloroform and 57 ml. of acetic acid under nitrogen and the temperature brought to 30°C. To this slurry is added 5.5 ml. of 9.6 N aqueous $H_2O_2$ (30%) 52.8 mmoles over 1 minute. The temperature is allowed to rise to 38°–40°C, then recooled over a half-hour period to 35°C. The batch is aged a total of 6.5 hours, maintaining 35°C internal temperature. After the age period, 175 ml. of water is added and the $CH\,CL_3$ layer concentrated to a small volume in vacuo. The residue is crystallized from 130 ml. of ethanol and the slurry aged 1.5 hours at 20°–25°C. The product is filtered and washed with 30 ml. of 2BA ethanol and dried in vacuo at 80°C. The product weighs 15.3 g. (86%), melting point 183°–185°C.

What is claimed is:

1. A process for preparing a compound of the formula:

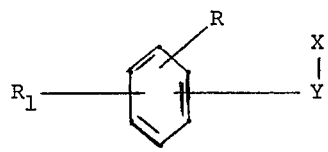

wherein Y is -$CH_2$ or -CH-$CH_3$; X is halogen and R and $R_1$ are each hydrogen, $C_{1-5}$ alkyl, $C_{1-5}$ alkylthio, $C_{1-5}$ alkoxy, hydroxy or halo, at least one of said R or $R_1$ being $C_{1-5}$ alkylthio, which comprises the steps of:

a. reacting at about 0°C to 40°C a benzene compound of the formula:

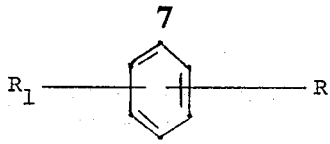

where R and $R_1$ are as defined above, with an alkane compound selected from the group consisting of di-$C_{1-5}$ alkoxymethane, di-$C_{1-5}$ alkoxyethane, di-$C_{7-10}$ aralkoxymethane and di-$C_{7-10}$ aralkoxyethane and a halogen containing Lewis acid to form a complex; and b. cleaving said complex to form the desired product.

2. The process of claim 1 wherein the alkane compound is di-$C_{1-5}$ alkoxymethane.

3. The process of claim 1 wherein the alkane compound is di-$C_{1-5}$ alkoxyethane.

4. The process of claim 1 wherein X is chloro or bromo and R and $R_1$ are each hydrogen, $C_{1-5}$ alkylthio, $C_{1-5}$ alkoxy or halo.

5. The process of claim 4 wherein R is hydrogen and $R_1$ is methylthio.

6. The process of claim 5 wherein the alkane compound is dimethoxymethane and the Lewis acid is $AlCl_3$ or $TiCl_4$.

7. The process of claim 6 wherein the Lewis acid is $AlCl_3$; the reaction is carried out in the presence of an inert solvent, the reaction temperature is between −15 and 80°C and the cleavage is carried out with water.

* * * * *